(12) United States Patent
Birkner et al.

(10) Patent No.: US 7,781,165 B2
(45) Date of Patent: Aug. 24, 2010

(54) BENZIMIDAZOLIUM COMPOUNDS AND SALTS OF BENZIMIDAZOLIUM COMPOUNDS FOR NUCLEIC ACID AMPLIFICATION

(75) Inventors: Christian Birkner, Uffing (DE); Frank Bergmann, Iffeldorf (DE); Herbert von der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 726 days.

(21) Appl. No.: 11/581,735

(22) Filed: Oct. 16, 2006

(65) Prior Publication Data
US 2007/0099220 A1 May 3, 2007

(30) Foreign Application Priority Data
Oct. 19, 2005 (EP) .................................. 05022774

(51) Int. Cl.
*C12Q 1/68* (2006.01)
*C12P 19/34* (2006.01)
*C07D 235/00* (2006.01)

(52) U.S. Cl. ........................ 435/6; 435/91.2; 548/304.4

(58) Field of Classification Search ........................ None
See application file for complete search history.

(56) References Cited

U.S. PATENT DOCUMENTS

| | | | | |
|---|---|---|---|---|
| 3,322,784 | A | * 5/1967 | Mohr et al. | ............... 548/304.4 |
| 5,118,801 | A | 6/1992 | Lizardi et al. | |
| 5,210,015 | A | 5/1993 | Gelfand et al. | |
| 5,449,603 | A | 9/1995 | Nielson et al. | |
| 5,487,972 | A | 1/1996 | Gelfand et al. | |
| 5,538,848 | A | 7/1996 | Livak et al. | |
| 5,563,037 | A | * 10/1996 | Sutherland et al. | ............. 435/6 |
| 5,693,502 | A | 12/1997 | Gold et al. | |
| 5,804,375 | A | 9/1998 | Gelfand et al. | |
| 6,174,670 | B1 | 1/2001 | Wittwer et al. | |
| 6,391,551 | B1 | 5/2002 | Shultz et al. | |
| 6,787,305 | B1 | 9/2004 | Li et al. | |
| 2005/0020814 | A1 | 1/2005 | Rudolph et al. | |

FOREIGN PATENT DOCUMENTS

| | | |
|---|---|---|
| EP | 0930370 A1 | 7/1999 |
| WO | WO 97/46707 | 12/1997 |
| WO | WO 97/46712 | 12/1997 |
| WO | WO 97/46714 | 12/1997 |
| WO | WO 99/46400 | 9/1999 |
| WO | WO 00/68411 | 11/2000 |
| WO | WO 01/02559 A1 | 1/2001 |
| WO | WO 02/14555 A2 | 2/2002 |

OTHER PUBLICATIONS

Bernard, P. et al., "Integrated Amplification and Detection of the C677T Point Mutation in the Methylenetetrahydrofolate Reductase Gene By Fluorescence Resonance Energy Transfer and Probe Melting Curves," Analytical Biochemistry 255, 101-107 (1998).
Cai, A. et al., "Quantitative Assessment of mRNA Cap Analogues as Inhibitors of in Vitro Translation," Biochemistry 1999, 38, 8538-8547.
Chakrabarti, R. et al., "The enhancement of PCR amplification by low molecule weight amides," Nucleic Acids Research, 2001, vol. 29, No. 11, 2377-2381.
Hayakawa, Y. et al., "Acid/Azole Complexes as Highly Effective Promoters in the Synthesis of DNA and RNA Oligomers via the Phosphoramidite Method," J. Am. Chem. Soc. vol. 123, No. 34, 2001, 8165-8176.
Hengen, P. et al., "Methods and Reagents," TIBS 22, Jun. 1997, 225-226.
Hildebrand, C. et al., "Differential Extraction of Histone H1 and Cooperative Removal of Histones from Chromatin," Biocheimica Biophysica Acta, 447(1977) 295-311.
Jemielity, J. et al., "Novel 'anti-reverse' cap analogs with superior translational properties," RNA (2003), 9:1108-1122.
Kainz, P. et al., "Specificity-Enhanced Hot-Start PCR: Addition of Double-Stranded DNA Fragments Adapted to the Annealing Temperature," BioTechniques, vol. 28, No. 2 (2000), 278-282.
Lin, Y. et al., "Inhibition of Multiple Thermostable DNA Polymerases by a Heterodimeric Aptamer," J. Mol. Biol. (1997) 271, 100-111.
Matthews, J. et al., "Analytical Strategies for the Use of DNA Probes," Analytical Biochemistry 169, 1-25(1988).
Sturzenbaum, S. et al., "Transfer RNA Reduces the Formation of Primer Artifacts During Quantitative PCR," BioTechniques 27:50-52 (Jul. 1999).
Tuntiwechapikul, W. et al., "DNA Modifications by 4-Aza-3-ene-1, 6-diynes: DNA Cleavage, pH-Dependent Cytosine-Specific Interactions, and Cancer Cell Cytotoxicity," Biochemistry 2002, 41, 5283-5290.
Kaboev, O.K. et al., Bioorg Khim 25 (1999) 398-400 (English Abstract).

* cited by examiner

*Primary Examiner*—Mark Staples
(74) *Attorney, Agent, or Firm*—Marilyn Amick; Roche Diagnostics Operations, Inc.

(57) ABSTRACT

The present invention is directed to the use of a benzimidazolium compound comprising a side chain at at least one of its N-residues, said chain being either a Cn-alkyl or a substituted Cn-alkyl, characterized in that preferably n is $\geq 3$, as an additive for a nucleic acid amplification reaction.

6 Claims, 7 Drawing Sheets

Figure 1a

Without compound 1

Figure 1b

With compound 1

BENZIMIDAZOLIUM COMPOUNDS AND SALTS OF BENZIMIDAZOLIUM COMPOUNDS FOR NUCLEIC ACID AMPLIFICATION

RELATED APPLICATIONS

This application claims priority to European application EP 05022774.3 filed Oct. 19, 2005.

FIELD OF THE INVENTION

The invention relates to the field of amplification of nucleic acids. More precisely, the invention provides compounds and methods for improvements of the polymerase chain reaction.

BACKGROUND OF THE INVENTION

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, for example, U.S. Pat. No. 6,174,670.

It is known for a long time that ionic concentration strongly affects the melting temperature of double stranded DNA hybrids. It is also known for a long time that metal ions or other ions are capable of binding to or interacting with nucleic acids and nucleic acid polymerases such as the thermostable Taq polymerase used for PCR. As a consequence, adding of such specific ions in many cases has been proven to have a strong impact on the performance of an amplification reaction. In particular, it is known that depending on the actual primer and target nucleic acid sequences, each different PCR reaction has a specific and very narrow optimum for its magnesium ion concentration.

A major problem with nucleic acid amplification and more especially with PCR is the generation of nonspecific amplification products such as the formation of primer/dimer artifacts. In many cases, this is due to a nonspecific oligonucleotide priming and subsequent primer extension event prior to the actual thermocycling procedure itself, since thermostable DNA polymerases are also moderately active at ambient temperature. For example, amplification products due to by chance occurring primer dimerization and subsequent extension are observed frequently.

Extension of non-specifically annealed primers has been shown to be inhibited by the addition of short double stranded DNA fragments (Kainz, P., et al., Biotechniques 28 (2000) 278-282). In this case, primer extension is inhibited at temperatures below the melting point of the short double stranded DNA fragment, but independent from the sequence of the competitor DNA itself. However, it is not known, to which extent the excess of competitor DNA influences the yield of the nucleic acid amplification reaction.

Alternatively, oligonucleotide aptamers with a specific sequence resulting in a defined secondary structure may be used. Such aptamers have been selected using the SELEX Technology for a very high affinity to the DNA polymerase (U.S. Pat. No. 5,693,502; Lin, Y., and Jayasena, S. D., J. Mol. Biol. 271 (1997) 100-111). The presence of such aptamers within the amplification mixture prior to the actual thermocycling process itself again results in a high affinity binding to the DNA polymerase and consequently a heat labile inhibition of its activity.

Due to the selection process, however, all so far available aptamers can only be used in combination with one particular species of DNA polymerase.

Oligonucleotide inhibitors (WO 01/02559) with blocked 3' end and 5' end were shown to enhance sensitivity and specificity of PCR reactions. They compete with the primer in binding to the polymerase.

It is also known that addition of single strand binding protein (U.S. Pat. No. 5,449,603) or tRNA (Sturzenbaum, S. R., Biotechniques 27 (1999) 50-52) results in non-covalent association of these additives to the primers. This association is disrupted when heating during PCR. It was also found that addition of DNA helicases prevent random annealing of primers (Kaboev, O. K., et al., Bioorg Khim 25 (1999) 398400). Furthermore, poly-glutamate (WO 00/68411) in several cases may be used in order to inhibit polymerase activity at low temperatures.

Other organic additives known in the art like DMSO, betaines, and formamides (WO 99/46400; Hengen, P. N., Trends Biochem. Sci. 22 (1997) 225-226; Chakrabarti, R., and Schutt, C. E., Nucleic Acids Res. 29 (2001) 2377-2381) result in an improvement of amplification of GC rich sequences, rather than prevention of unspecific priming. Similarly, heparin may stimulate in vitro run-on transcription presumably by removal of proteins like histones in order to make chromosomal DNA accessible (Hildebrand, C. E., et al., Biochimica et Biophysica Acta 477 (1977) 295-311). In particular, WO 99/46400 discloses the beneficial effects on PCR performance of adding compounds such as 4-methylmorpholine N-oxide, betaine, and N-alkylimidazoles such as proline, 1-methylimidazole or 4-methylimidazole.

Yet, unfortunately, none of the PCR additives disclosed in the art so far is capable of providing an absolute specificity for primer annealing while maintaining sufficient sensitivity.

Thus, there is a need in the art to provide an alternative PCR method, which is cheap, easy to perform, and—most important—which does improve the performance of the PCR reaction itself.

BRIEF DESCRIPTION OF THE INVENTION

Thus, the present invention is directed to the use of a benzimidazolium compound comprising a side chain at at least one of its N-residues, said chain being either a Cn alkyl or a substituted Cn alkyl, as an additive for a nucleic acid amplification reaction characterized in that preferably n is $\geq 3$.

In one embodiment, the present invention is directed to the use of a benzimidazolium compound comprising a side chain at at least one of its N-residues, said chain being either a Cn alkyl or a substituted Cn alkyl, characterized in that n is $\geq 3$ wherein said benzimidazolium compound has the formula Formula I characterized in that R1 and R2 are independently selected from a group consisting of H, C1 alkyl, C2 alkyl, C3 alkyl, C4 alkyl, —(CH2)$_o$—O—(CH2)$_p$-H, wherein o+p is ≦3, Formula II or Formula III wherein q is ≦6, and R3=C1-4 alkyl.

In a particular embodiment, said benzimidazolium compound is 3-ethyl-1-[4-(3-ethyl-3H-benzimidazol-1-ium)-but-1-yl]3H-benzimidazol-1-ium.

It has been proven to be advantageous if said particular benzimidazolium compounds are added to the amplification mixture as salts with either a sulfonate or a halogenide as a counter-ion.

Addition of the compounds disclosed above may in general be used in order to decrease nucleotide base pairing interactions, to decrease the melting temperature of an amplification product.

Addition of the compounds disclosed above to an amplification reaction mixture may also be used in order to enhance the efficiency of an amplification reaction and a particular amplification reaction wherein said amplification is monitored in real time.

Furthermore, it is also within the scope of the present invention, if a compound as disclosed above is used as an additive for a nucleic acid melting point determination of an amplification product or a probe-target nucleic acid hybrid.

In another aspect, the present invention is also directed to a composition comprising all components necessary to perform a nucleic acid reaction and a compound disclosed above.

In yet another aspect, the present invention is directed to a kit comprising a composition with components necessary to perform a nucleic acid reaction and a compound disclosed above.

BRIEF DESCRIPTION OF THE DRAWINGS

A (5×106 copies): specific PCR product formation

B (5×10 copies): Primer/dimer formation with lower melting point

A (5×10 copies): specific PCR product formation

C (5×10 copies): specific PCR product formation

| lane | Annealing temperature | |
|---|---|---|
| 1 (DNA marker) | | Without compound 2 |
| 2 | 49° C. | |
| 3 | 50° C. | |
| 4 | 51° C. | |
| 5 | 53° C. | |
| 6 | 55° C. | |
| 7 | 49° C. | With compound 2 |
| 8 | 50° C. | |
| 9 | 51° C. | |
| 10 | 53° C. | |
| 11 | 55° C. | |

A: target band

B: non specific PCR products

C: primer/dimer

FIGS. 3a, b, and c: Improvement of sensitivity and PCR efficiency:

DETAILED DESCRIPTION OF THE INVENTION

Use of a benzimidazolium compound comprising a side chain at at least one of its N-residues, said chain being either a Cn alkyl or a substituted Cn alkyl, characterized in that n is ≧3, enhances the efficiency, sensitivity and specificity of the amplification reaction. Increase of amplification efficiency is observed by the fact that addition of such a benzimidazolium, a typical amplification reaction results in an increase in the amount of finally synthesized amplification product and/of synthesis of a certain amount of an amplification product is achieved at earlier amplification cycles. Increase in amplification specificity is observed by the fact that addition of such a benzimidazolium results in a reduced synthesis of unspecific amplification products such as primer/dimers.

Moreover, the presence of such benzimidazolium salts facilitates the design and optimization of conditions of new assays, because inhibitory effects due to anorganic cations can be eliminated.

Different Derivative Embodiments of Benzimidazolium which May be Used According to the Present Invention According to the present invention, it is advantageous to use any kind of benzimidazolium compound comprising a side chain at at least one of its N-residues, said chain being either a Cn alkyl or a substituted Cn alkyl, characterized in that n is ≧3.

Preferably, such compounds have the generic formula

Formula I characterized in that R1 is either a Cn alkyl or a substituted Cn alkyl, characterized in that n is $\geq 3$. R2 is selected from H, a Cn alkyl or a substituted Cn alkyl, characterized in that n is $\geq 3$.

More preferably, such compounds have the formula

Formula I characterized in that R1 and a R2 are independently selected from a group consisting of H, C1 alkyl, C2 alkyl, C3 alkyl, C4 alkyl, —$(CH2)_o$-O—$(CH2)_p$-H, wherein o+p is $\leq 3$, Formula II Formula III wherein q is $\leq 6$, but preferably 4, and R3=C1-C4 alkyl, with the proviso that at least one of R1 and R2 is either a Cn alkyl or a substituted Cn alkyl, characterized in that n is $\geq 3$.

In one particular embodiment, said benzimidazolium compound is a mono-benzimidazolium compound characterized in that R1 is H or C1-C4 alkyl, and R2 is C1-C4 alkyl, for example, 1-methyl-3-propyl-benzimidazolium or 1-butyl-3-methyl-benzimidazolium.

In another particular embodiment, said benzimidazolium compound is a bis-benzimidazolium compound, characterized in that R1 is a C1-C4 alkyl and R2 is a C1-C6 chain which at the distal C-atom is substituted with a second Imidazole or benzimidazole group. Examples for this particular embodiment are 3-ethyl-1-[4-(3-ethyl-3H-benzimidazol-1-ium)but-1-yl]-3H benzimidazol-1-ium, 3-methyl-1-[4-(3-methyl-3H-benzimidazol-1-ium)but-1-yl]-3H benzimidazol-1-ium.

In an alternative embodiment, in such a compound according to Formula I, both R1 and R2 are —$CH_3$. Such a molecular structure provides the molecule with a sufficient degree of hydrophobicity necessary to achieve the desired performance of enhancing a PCR reaction.

It has been proven to be advantageous if said particular benzimidazolium compounds are added to the amplification mixture as salts, with either a sulfonate or a halogenide as a counter-ion. Preferably, the sulfonate is a toluylsulfate or a ditoluylsulfate. Also preferably, the halogenide is an iodine.

Those salts are either commercially available from companies such as Sigma or may be synthesized according to standard chemistry methods known in the art.

However, it is also within the scope of the present invention in case the benzimidazolium compounds disclosed above are added to the amplification mixture as uncharged compounds, as long as they are dissolvable.

All compounds disclosed above have been proven to be advantageous for the following applications, uses, compositions, reaction mixtures and kits.

Different uses of a benzimidazolium compounds comprising a side chain at at least one of its N-residues, said chain being either a Cn alkyl or a substituted Cn alkyl, characterized in that n is ☐3

Preferably, the nucleic acid amplification reaction is a polymerase chain reaction using a forward and a reverse primer, a thermostable DNA polymerase and nucleoside triphosphates in order to generate an amplification product during an adjusted thermocycling protocol comprising a primer annealing phase, a primer elongation phase and a denaturation phase. Also preferably, the compound according to the invention is added to the amplification mixture in the form of a salt.

The enhancement of specificity of the PCR reaction may probably be due to inhibition of primer/dimer formation as will be shown in some of the examples. In case a primer concentration is used in a range that primer annealing is a rate limiting step of the amplification reaction, this inhibition of primer/dimer formation may also lead to an increased sensitivity of detecting a target nucleic acid of low abundance.

The exact final concentration optimum of the specific benzimidazole that may be used according to the invention, however, may vary dependent on the exact benzimidazole derivative that is used and also depending on the nature of the other compounds of the amplification mixture.

It is also within the scope of invention, if a specific benzimidazole used according to the invention is added to an RT-PCR reaction, characterized in that an RNA template sequence is amplified. RT-PCR can be performed according to different protocols, wherein first strand and second strand synthesis are either performed by two different enzymes or by using the same enzyme for both steps.

For the first strand synthesis, any kind of RNA dependent DNA polymerases (reverse transcriptase) may be used, e.g. AMV reverse transcriptase or MMLV reverse transcriptase. Subsequently, the RNA/cDNA hybrid is subjected to thermal denaturation or alternatively, the RNA template within the hybrid may be digested by RNaseH. Second strand synthesis and amplification may then be performed in the presence of an additive with any kind of thermostable DNA dependent DNA polymerase like e.g. Taq DNA polymerase according to standard protocols.

Alternatively, for an approach where first and second strand synthesis is done with one enzyme, thermostable DNA polymerases like *Thermus thermophilus* or C. Therm (Roche Diagnostics) may be used in the presence of an additive according to the invention.

In one specific embodiment, the specific benzimidazole that is used according to the invention may be used as an additive to a Real Time PCR amplification mixture. In such a kinetic approach, the formation of PCR products is usually measured in thermocyclers which have additional devices for monitoring fluorescence signals during the amplification reaction.

For example, fluorescently labeled hybridization probes may be used for real time monitoring. Those hybridization probes used for the inventive method according to the invention are usually single-stranded nucleic acids such as single-stranded DNA or RNA or derivatives thereof or alternatively LNAs or PNAs which hybridize at the annealing temperature of the amplification reaction to the target nucleic acid. These oligonucleotides usually have a length of 20 to 100 nucleotides.

The labeling can be introduced on any ribose or phosphate group of the oligonucleotide depending on the particular detection format. Labels at the 5' and 3' end of the nucleic acid molecule are preferred.

The type of label must be detected in the real-time mode of the amplification reaction. This is not only possible for fluorescently labeled probes but also possible with the aid of labels that can be detected by NMR. Methods are particularly preferred, however in which the amplified nucleic acids are detected with the aid of at least one fluorescent-labelled hybridization probe.

Many different test procedures are possible. The following detection formats are particularly useful in connection with the use of a benzimidazolium compound comprising a side chain at at least one of its N-residues, said chain being either a Cn alkyl or a substituted Cn alkyl, characterized in that n is $\geq 3$:

Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

FRET Hybridization Probes

The FRET Hybridization Probe test format is especially useful for all kinds of homogenous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. Among all detection formats known in the art of real time PCR, the FRET-Hybridization Probe format has been proven to be highly sensitive, exact and reliable (WO 97/46707; WO 97/46712; WO 97/46714). As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

Besides PCR and real time PCR, FRET hybridization probes are used for melting curve analysis. In such an assay, the target nucleic acid is amplified first in a typical PCR reaction with suitable amplification primers. The hybridization probes may already be present during the amplification reaction or added subsequently. After completion of the PCR-reaction, the temperature of the sample is constitutively increased, and fluorescence is detected as long as the hybridization probe was bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed.

If during such a melting curve analysis, a benzimidazole comprising a side chain at least one of its N-residues, said chain being either a Cn-alkyl or a substituted Cn-alkyl, characterized in that n is $\geq 3$ is present within the sample, much sharper curves are obtained, when the first derivative of a respective fluorescence versus temperature-time plot is determined.

Single Label Probe (SLP) Format

This detection format consists of a single oligonucleotide labeled with a single fluorescent dye at either the 5'- or 3'-end (WO 02/14555). Two different designs can be used for oligo labeling: G-quenching probes and nitroindole-dequenching probes. In the G-quenching embodiment, the fluorescent dye is attached to a C at oligo 5'- or 3'-end. Fluorescence decreases significantly when the probe is hybridized to the target, in case two G's are located on the target strand opposite to C and in position 1 aside of complementary oligonucleotide probe. In the nitroindole dequenching embodiment, the fluorescent dye is attached to nitroindole at the 5'- or 3'-end of the oligonucleotide. Nitroindole somehow decreases the fluorescent signaling of the free probe. Fluorescence increases when the probe is hybridized to the target DNA due to a dequenching effect.

TAQMAN (Roche Molecular Systems) Probe

A single-stranded hybridization probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq polymerase during the subsequent elongation phase. As a result the excited fluorescent component and the quencher are spatially separated from one another and thus a fluorescence emission of the first component can be measured. TAQMAN probe assays are disclosed in detail in U.S. Pat. Nos. 5,210,015, 5,538,848, and 5,487,972. TAQMAN hybridization probes and reagent mixtures are disclosed in U.S. Pat. No. 5,804,375.

Releasing Formats

Moreover, two other formats restricted to allele specific detection have been disclosed recently which are based on the principle of specific detection of a release of a labeled 3' terminal nucleotide due to a match or mismatch situation regarding its binding to the target nucleic acid. U.S. Pat. No. 6,391,551 discloses a method, characterized in that the 3' terminal nucleotide of a hybridization probe is released by a depolymerizing enzyme in case a perfect match between target sequence and probe has occurred. Similarly, EP 0 930 370 suggests to use a primer labeled with a reporter and a quencher moiety, characterized in that a 3'-5' proofreading activity removes one moiety in case no perfect match between primer and amplification target has occurred.

SYBR Green Format

It is also within the scope of the invention, if real time PCR is performed in the presence of an additive according to the invention in case the amplification product is detected using a double stranded nucleic acid binding moiety. For example, the respective amplification product can also be detected according to the invention by a fluorescent DNA binding dye which emits a corresponding fluorescence signal upon interaction with the double-stranded nucleic acid after excitation with light of a suitable wavelength. The dyes SYBR Green I and SYBR Gold (Molecular Probes) have proven to be particularly suitable for this application. Intercalating dyes can alternatively be used. However, for this formate, in order to discriminate the different amplification products, it is necessary to perform a respective melting curve analysis (U.S. Pat. No. 6,174,670).

Due to the fact that real time amplicon detection with this format can not discriminate between specific products and amplification artifacts such as primer/dimers, a subsequent melting curve analysis is usually performed. After completion of the PCR reaction, the temperature of the sample is constitutively increased, and fluorescence is detected as long as SYBR Green is bound to the double stranded DNA present in the samples. Upon dissociation of the double stranded DNA the signal decreases immediately. This decrease is monitored with an appropriate fluorescence versus temperature-time plot such that a first derivative value can be determined, at which the maximum of fluorescence decrease is observed. Since short primer/dimer double stranded DNAs are usually short, dissociation into single stranded DNA occurs at lower temperatures as compared to the dissociation of the double stranded specific amplification product.

If during such a melting curve analysis, a benzimidazolium compound comprising a side chain at at least one of its N-residues, said chain being either a Cn-alkyl or a substituted Cn-alkyl, characterized in that n is $\geq 3$ is present within the sample, much sharper curves are obtained in many cases, when the first derivative of a respective fluorescence versus temperature-time plot is determined. In particular, this is true for those embodiments, wherein bis-benzimidazolium compounds according to the invention are used.

In another embodiment of the invention which may also include real time monitoring, the amplification reactions are performed in the presence of an additive according to the invention by means of rapid thermocycling, wherein one cycle is less than one minute. The instrumental basis for such a rapid thermocycling is provided e.g. by the LIGHTCYCLER (Roche Diagnostics GmbH) and disclosed in WO 97/46707 and WO 97/46712. According to the present invention, the annealing of primers is not the rate limiting step of quantitative amplification of target nucleic acids being present in the sample with only low abundance. Therefore, the time parameters for a respective multiplex thermocycling protocol in order to amplify low abundance parameters don't need to be amended as compared to any kind of thermocycling protocols known in the art.

It is also within the scope of the present invention, if a benzimidazolium compound comprising a side chain at at least one of its N-residues, said chain being either a Cn-alkyl or a substituted Cn-alkyl, characterized in that n is $\geq 3$ is used as an additive for a mixture containing nucleic acids in order to decrease nonspecific hybridization effects by a slowed down amplicon reannealing. Besides its positive effect on prevention of primer dimer formation in a hot start PCR approach, addition of such a benzimidazole also may enhance specificity of any kind of analytical hybridization method like, e.g. Southern blot analysis, Northern Blot analysis, Dot blot analysis etc.

In a still other aspect of the invention, such a benzimidazolium compound comprising a side chain at at least one of its N-residues, said chain being either a Cn-alkyl or a substituted Cn-alkyl, characterized in that n is $\geq 3$ may be used as an additive for determination of nucleic acid melting points, i.e. determination of melting temperatures at which an at least partially double stranded nucleic acid hybrid molecule denatures into two single stranded molecules independently from a real time PCR reaction.

In yet another aspect, the new invention is directed to a composition or a reaction mixture comprising components necessary to perform a nucleic acid amplification reaction and a benzimidazolium compound comprising a side chain at at least one of its N-residues, said chain being either a Cn alkyl or a substituted Cn alkyl, characterized in that n is $\geq 3$. In one embodiment, the inventive composition is a generic composition, which comprises all necessary components for nucleic acid amplification but lacks specific amplification primers. In a second embodiment, the inventive composition or reaction mixture is a parameter specific composition which comprises all components necessary to perform a specific amplification reaction including a specific pair of amplification primers. In a third embodiment, a composition or reaction mixture according to the second embodiment additionally comprises detection moieties like suitable fluorescent hybridization probes or ds nucleic acid binding compounds such as SYBR Green. In a forth embodiment, a composition or reaction mixture according to the third embodiment additionally comprises a nucleic acid sample from which the target nucleic acid shall become amplified.

Similarly, the invention is directed to a kit comprising a composition with all components necessary to perform a nucleic acid reaction in the presence of a benzimidazolium compound comprising a side chain at at least one of its N-residues, said chain being either a Cn alkyl or a substituted Cn-alkyl, characterized in that n is $\geq 3$. Preferably, these kits comprise compositions disclosed as embodiments 1, 2 and 3 above. Alternatively, the components necessary for amplification and the additive according to the invention may be present in different storage vessels.

SPECIFIC EMBODIMENTS

Example 1

Synthesis of Methyl-Butyl-Benzimidazolium-Toluenesulfate (Compound 1)

20.0 g of benzimidazole (169 mmol) and 26.4 g of methyliodine (186 mmol) were dissolved in 100 ml of acetonitrile and refluxed for 7 hours. After removal of the solvent under vacuum the residue was purified with silica gel (ethylacetate/petroleum 9:1).

3.2 g of butanole (43.2 mmol) were dissolved in 80.0 ml of pyridine and 9.47 g of toluylsulfochloride (49.7 mmol) were added slowly at 0° C. After stirring for 3 hours at 0° C. the reaction mixture was added to 400 ml of ice water and 30.0 ml of 2N HCl were added. The organic phase was separated and dissolved in ethylacetate. The organic phase was washed with 2N HCl and dried over magnesium sulfate. After removal of the solvent the butylsulfonate was directly used without further purification.

1.8 g of methylbenzimidazole (13.6 mmol) and 3.11 g of toluene sulfobutyrate (13.6 mmol) were added to 30.0 ml of acetonitrile and refluxed for 24 hours. The solvent was removed under reduced pressure and the residue was dissolved in 70.0 ml of diethylether. After filtration the residue was washed subsequently with diethylether and ethylacetate. After removal of the solvent 4.64 g (12.9 mmol) crystalline powder were received.

Yield 64%

$^1$H-NMR: (300 MHz, DMSO-$d_6$):

9.7 (s, 1H), 8.1 (dd, 2H), 7.7 (m, 2H), 7.5 (d, 2H), 7.10 (d, 2H), 4.48 (t, 2H), 4.07 (s, 1H), 2.29 (s, 3H), 1.86 (m, 2H), 1.35 (m, 2H), 0.94 (t, 3H)

Formula IV (Compound 1)

Example 2

Improvement of Sensitivity/Specificity of a One Step RT-PCR

Two different kits were used for this experiment:

LC-Transkriptor first strand cDNA synthesis kit (Cat-no: 04379012001 Roche Diagnostics GmbH) containing the EnzymeMix LC-h-G6PDH Housekeeping Gene Set (Cat-no: 03261883001 Roche Diagnostics GmbH) containing the PrimerMix and the target G6PDH RNA, MgCl$_2$ and water.

Six serial single dilutions of the G-6-PDH RNA standard were prepared with concentrations of c=5×10$^6$ copies/5 μl, ×10$^5$ copies/5 μl, 5×10$^4$ copies/5 μl, 5×10$^3$ copies/5 μl, 5×10$^2$ copies/5 μl and 5×10$^6$ copies/5 μl in PCR grade water.

PCR was carried out with LIGHTCYCLER instrument (Roche Diagnostics GmbH) in the presence or absence of 10 mM compound 1 of Example 1.

Values for denaturation, amplification and melting curve analysis were programmed as follows:

Pipetting Scheme for Mastermix: for 1 Reaction in 20 μl Capillaries

| Component | volume |
| --- | --- |
| H$_2$O | 7.8 μl |
| MgCl$_2$ (25 mM) | 0.8 μl |
| G6PDH Primer (detection mix) | 2.0 μl |
| LC RT-PCR Enzyme mix (E1) | 0.4 μl |
| LC RT-PCR Reaction mix (P6) | 4.0 μl |
| Volume | 15 μl |

5 μl of the standard were added: total volume: 20 μl

Program 1: Reverse Transcription

| Cycle Program Data | Value |
| --- | --- |
| Cycles | 1 |
| Analysis Mode | None |
| Temperature Targets | Segment 1 |
| Target temperature | 55 |
| Incubation time (min:s) | 10:00 |
| Temperature transition rate (° C./s) | 20 |
| Secondary target temperature (° C.) | 0 |
| Step size (° C.) | 0 |
| Step delay (cycles) | 0 |
| Acquisition mode | None |

Program 2: Denaturation

| Cycle Program Data | Value |
| --- | --- |
| Cycles | 1 |
| Analysis Mode | None |
| Temperature Targets | Segment 1 |
| Target temperature | 95 |
| Incubation time (min:s) | 30 |
| Temperature transition rate (° C./s) | 20 |
| Secondary target temperature (° C.) | 0 |
| Step size (° C.) | 0 |
| Step delay (cycles) | 0 |
| Acquisition mode | None |

Program 3: Amplification

| Cycle Program Data | Value | | |
| --- | --- | --- | --- |
| Cycles | 45 | | |
| Analysis Mode | Quantification | | |
| Temperature Targets | Segment 1 | Segment 2 | Segment 3 |
| Target temperature | 95 | 55 | 72 |
| Incubation time (s) | 0 | 10 | 13 |
| Temperature transition rate (° C./s) | 20 | 20 | 2 |
| Secondary target temperature (° C.) | 0 | 0 | 0 |
| Step size (° C.) | 0 | 0 | 0 |
| Step delay (cycles) | 0 | 0 | 0 |
| Acquisition mode | None | None | Single |

Program 4: Melting Curve

| Cycle Program Data | Value | | |
|---|---|---|---|
| Cycles | 1 | | |
| Analysis Mode | Melting curve | | |
| Temperature Targets | Segment 1 | Segment 2 | Segment 3 |
| Target temperature | 95 | 65 | 95 |
| Incubation time (s) | 0 | 10 | 0 |
| Temperature transition rate (° C./s) | 20 | 20 | 0.1 |
| Secondary target temperature (° C.) | 0 | 0 | 0 |
| Step size (° C.) | 0 | 0 | 0 |
| Step delay (cycles) | 0 | 0 | 0 |
| Acquisition mode | None | None | Cont |

Program 5: Cooling

| Cycle Program Data | Value |
|---|---|
| Cycles | 1 |
| Analysis Mode | None |
| Temperature Targets | Segment 1 |
| Target temperature | 40 |
| Incubation time (min:s) | 30 |
| Temperature transition rate (° C./s) | 20 |
| Secondary target temperature (° C.) | 0 |
| Step size (° C.) | 0 |
| Step delay (cycles) | 0 |
| Acquisition mode | None |

Reaction was monitored in real time using the SYBR Green modus of the LIGHTCYCLER instrument and crossing points were determined according to the manufacturer's instructions. The crossing points obtained in relation to the target concentration is shown in the following table.

| Target concentration (copies) | Crossing point in the absence of compound 1 | Crossing point in the presence of compound 1 |
|---|---|---|
| $5 \times 10^6$ | 16.76 | 17.33 |
| $5 \times 10^5$ | 19.65 | 20.89 |
| $5 \times 10^4$ | 21.08 | 24.13 |
| $5 \times 10^3$ | 21.24 | 26.48 |
| $5 \times 10^2$ | 21.03 | 27.79 |
| $5 \times 10$ | 21.87 | 28.12 |

Table: crossing points (Cp values) of different target concentrations in the presence and absence of Compound 1 (SYBR Green detection format.) in a real time PCR experiment.

Figure 1A:
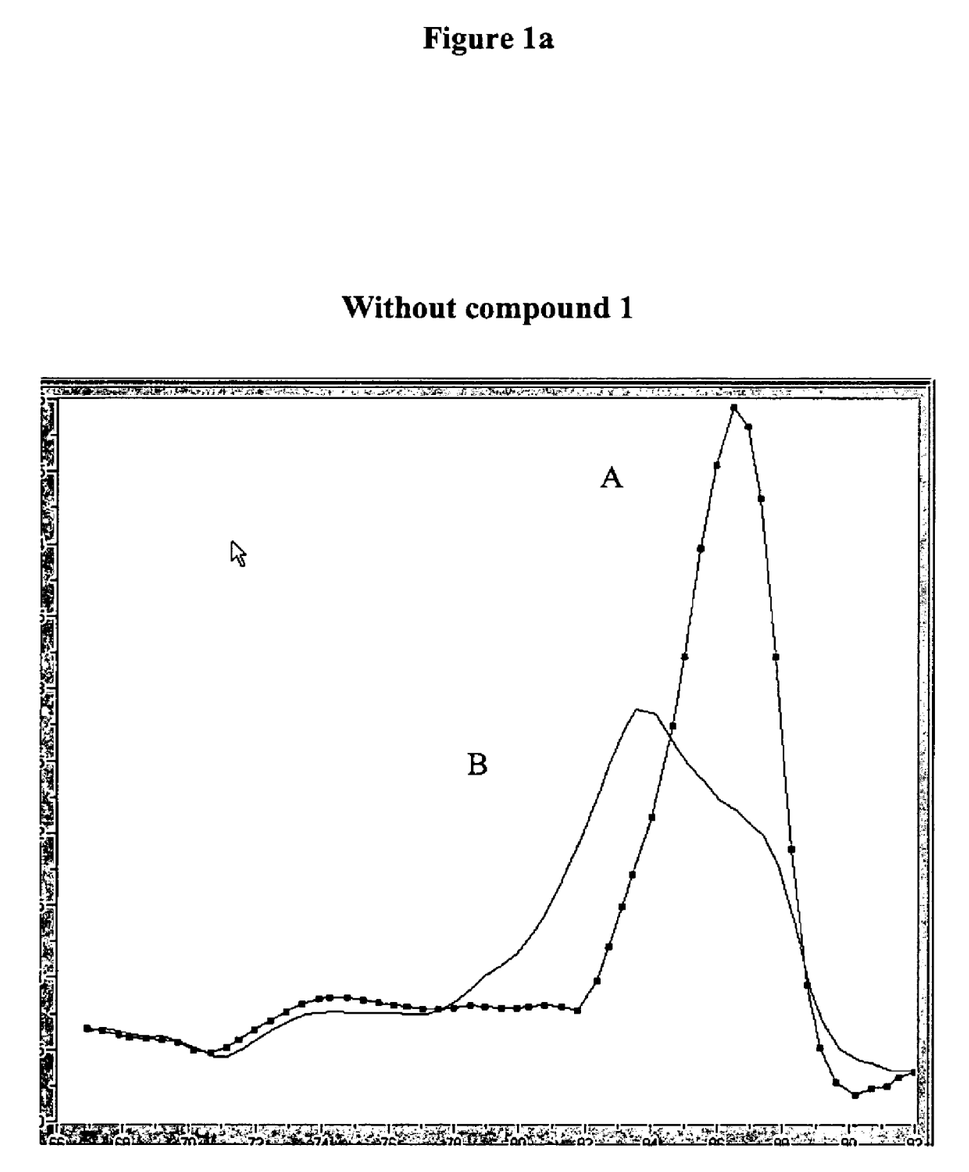
FIG. 1a: Melting curve analysis of PCR reaction without compound 1
Figure 1B:
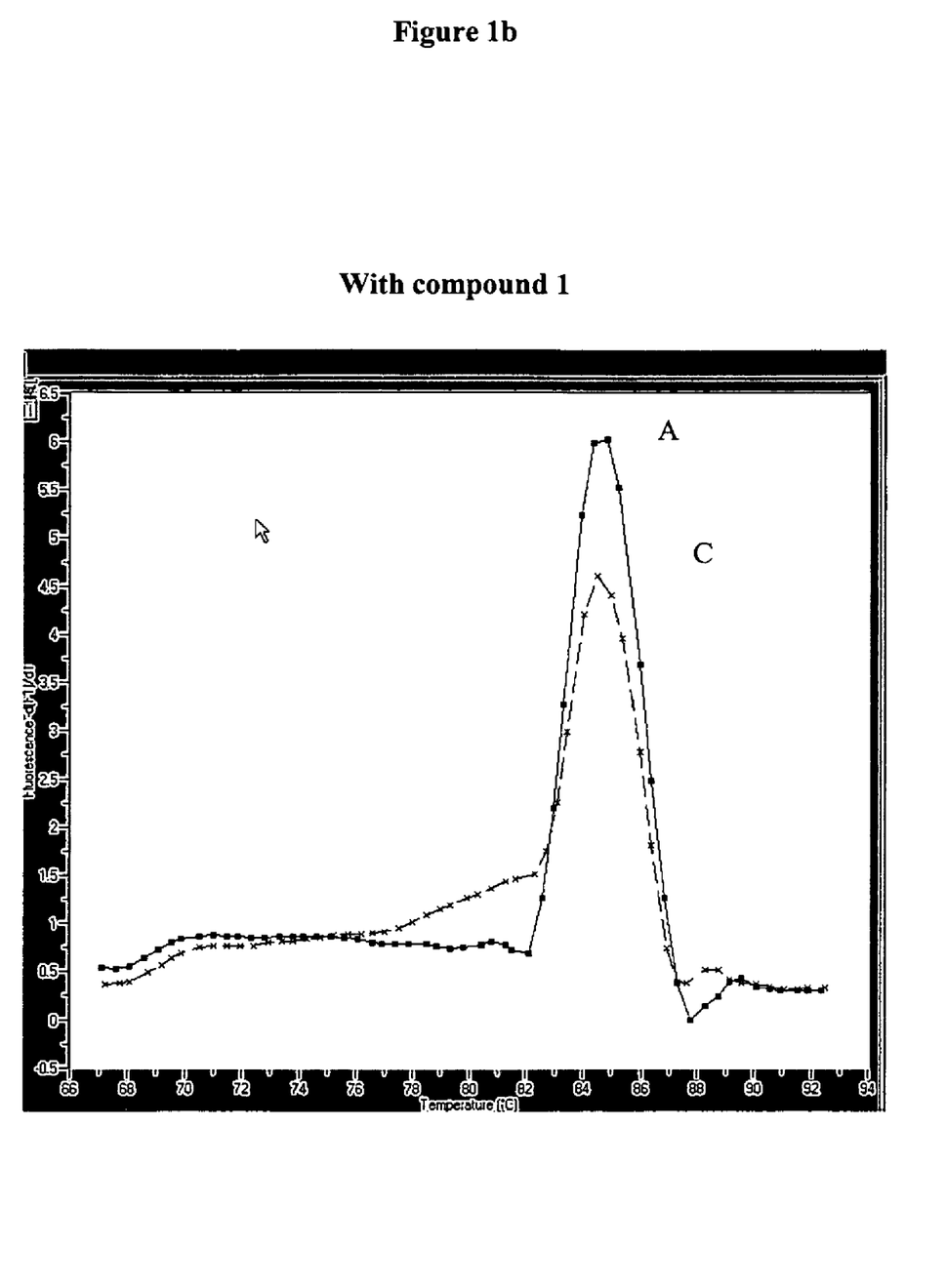
FIG. 1b: Melting curve analysis of PCR reaction with compound 1

Due to the impossibility to distinguish specific and non-specific PCR product formation in a Sybr Green format the validity of the RT-PCR reaction was confirmed by melting curve analysis on the LIGHTCYCLER instrument according the manufacturer's instructions (FIGS. 1a and 1b). As can be seen below at a target concentration of $5 \times 10^4$ copies a strong primer/dimer formation with a lower melting point was observed (FIG. 1a) without compound 1. In the presence of compound 1 the primer/dimer formation was strongly reduced (FIG. 1b). Even in a target concentration of $5 \times 10$ copies specific PCR product formation was observed.

Example 3

Improvement of Specificity of the Long Template PCR

For this experiment we used compound 2 (SIGMA (Cat-no.: L203599) and the Expand High Fidelity PCR System (Roche Diagnostics GmbH, Catalog number 1732650) containing Expand High Fidelity Enzyme mix, Expand High Fidelity buffer (10×) with 25 mM MgCl2 and PCR Nucleotide Mix (Roche Diagnostics GmbH, Catalog number 11814362) containing PCR Nucleotide Mix 10 mM were used.

Primers were

```
Primer Roche (10 µM)
5'-GAG GTC CGG CAG CGT CAG G-3'    (SEQ ID NO: 1)

Primer Roche (10 µM)
5'-CGC AGG TCG CGA CGC AAC G-3'    (SEQ ID NO: 2)
```

PCR was carried out with a blockcycler instrument in the presence or absence of 0.1 mM compound 2 according to Formula V.

Formula V (Compound 2)

As a template 2.8 kb fragment, GC-rich template of plant genomic DNA sequence amplifiable from whole genomic DNA with

```
primers Roche F1
CAG GTG GAA GGT GCG TCC GTT G    (SEQ ID NO: 3)
and

Roche R1
CTT CTC CCT CTG TGG CCT TCA C    (SEQ ID NO: 4)
``` was used with a concentration of c=0.1 ng/µl.

Values for denaturation and amplification were programmed as follows:

| | | | |
|---|---|---|---|
| Denaturation: | 94° C. | 2 min | |
| Amplification: | 94° C. | 15 sec | |
| | 50–60° C. | 30 sec | } 30x |
| | 72° C. | 3.3 min | |
| Elongation: | 72° C. | 7 min | |
| Cooling: | 8° C. | forever | |

Pipetting Scheme for Mastermix: for 1 Reaction in PCR-Tubes

| Component | Volume |
|---|---|
| H$_2$O | 39.25 |
| dNTP's, 10 mM | 1.0 µl |
| Primer A F3 [10 µM] | 1.5 µl |
| Primer B R3 [10 µM] | 1.5 µl |
| 10x Puffer + MgCl2 pH 8.9 | 5.0 µl |
| EnzymHiFi | 0.75 µl |
| Template 0.1 ng/µl | 1.0 µl |
| Total volume | 50 µl |

PCR was performed in the presence or absence of compound 2. The PCR-products were applied to a 1% agarose gel with ethidiumbromide staining.

Figure 2:
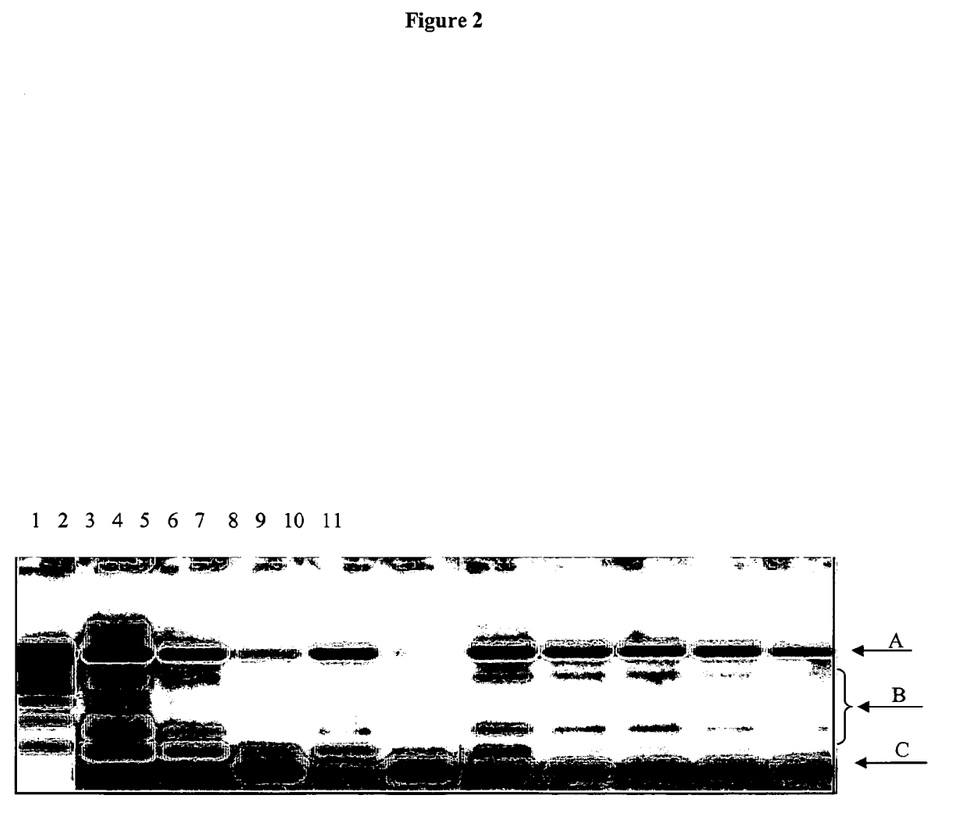
FIG. 2: Gel electrophoresis of long template PCR product (1% Agarose)

Results are shown in FIG. 2. As can be seen in the figure an improved specificity and the reproducibility over a broader annealing temperature region for the target is reached in the presence of 0.1 mM of Compound 2.

Example 4

Improvement of Sensitivity and PCR Efficiency with Taq Polymerase

For this experiment two Kits: LC-Faktor V Leiden Mutation Detection (Cat-no: 2212161 Roche Diagnostics GmbH) containing the standard DNA and LIGHTCYCLER DNA Master HYBPROBE (Cat-no.: 12158825-001 Roche Diagnostics GmbH) containing PCR-grade water, 25 mM MgCl2 PCR-grade and 10× Reaction Mix, were used.

The following primers and probes were used:

```
Primer Factor V fwd.
5'-GAG AGA CAT CGC CTC TGG GCT A-3'    (SEQ ID NO: 5)

Primer Factor V rev.
5'-TGT TAT CAC ACT GGT GCT AA-3'       (SEQ ID NO: 6)

Probe Factor V Fluos
5'-AAT ACC TGT ATT CCT CGC CTG TC-     (SEQ ID NO: 7)
Fluorescein-3'

Probe Factor V LC-Red-640:
5'-LC-Red-640-NH(CH2)6-AGG-GAT CTG     (SEQ ID NO: 8)
CTC TTA CAG ATT AGA AGT AGT CCT ATT-
p-3'
```

A 10× Primer Mix with c=5 µM/L, a 10× Fluos Mix with c=2 µM/L and a 10× Red-640 Mix with c=2 µM/L was prepared. The standard from LC-Faktor V Leiden Mutation Detection Kit was diluted to 50 pg/µl, 5 pg/µl, 500 fg/µl, 50 fg/µl, 5 fg/µl and 0.5 fg/µl.

PCR was performed with LIGHTCYCLER instrument (Roche Diagnostics GmbH) in the presence or absence of 20 mM of Compound 1 and in the presence or absence of 1 mM of Compound 2 according to Formulas IV and V (see Examples 1 and 3)

Values for denaturation, amplification and melting curve analysis were programmed as follows:

Pipetting Scheme for Mastermix: for 1 Reaction in 20 µl Capillaries

| Component | Volume |
|---|---|
| H2O | 5.4 µl |
| MgCl | 1.6 µl |
| Reactionmix | 2.0 µl |
| 10 × Primer | 2.0 µl |
| 10 × Probe Fluos | 2.0 µl |
| 10 × Probe Red-640 | 2.0 µl |
| Volume | 15 µl |

5 µl of the standard were added: total volume: 20 µl

Program 1: Denaturation

| Cycle Program Data | Value |
|---|---|
| Cycles | 1 |
| Analysis Mode | None |
| Temperature Targets | Segment 1 |
| Target temperature | 95 |
| Incubation time (min:s) | 30 |
| Temperature transition rate (° C./s) | 20 |
| Secondary target temperature (° C.) | 0 |
| Step size (° C.) | 0 |
| Step delay (cycles) | 0 |
| Acquisition mode | None |

Program 2: Amplification

| Cycle Program Data | Value | | |
|---|---|---|---|
| Cycles | 45 | | |
| Analysis Mode | Quantification | | |
| Temperature Targets | Segment 1 | Segment 2 | Segment 3 |
| Target temperature | 95 | 55 | 72 |
| Incubation time (s) | 0 | 10 | 10 |
| Temperature transition rate (° C./s) | 20 | 20 | 20 |
| Secondary target temperature (° C.) | 0 | 0 | 0 |
| Step size (° C.) | 0 | 0 | 0 |
| Step delay (cycles) | 0 | 0 | 0 |
| Acquisition mode | None | Single | None |

Program 3: Melting Curve

| Cycle Program Data | Value | | |
|---|---|---|---|
| Cycles | 1 | | |
| Analysis Mode | Melting curve | | |
| Temperature Targets | Segment 1 | Segment 2 | Segment 3 |
| Target temperature | 95 | 45 | 80 |
| Incubation time (s) | 0 | 60 | 0 |
| Temperature transition rate (° C./s) | 20 | 20 | 0.1 |
| Secondary target temperature (° C.) | 0 | 0 | 0 |
| Step size (° C.) | 0 | 0 | 0 |
| Step delay (cycles) | 0 | 0 | 0 |
| Acquisition mode | None | None | Cont |

Program 4: Cooling

| Cycle Program Data | Value |
|---|---|
| Cycles | 1 |
| Analysis Mode | None |
| Temperature Targets | Segment 1 |
| Target temperature | 40 |
| Incubation time (min:s) | 30 |
| Temperature transition rate (° C./s) | 20 |
| Secondary target temperature (° C.) | 0 |
| Step size (° C.) | 0 |
| Step delay (cycles) | 0 |
| Acquisition mode | None |

Figure 3A:
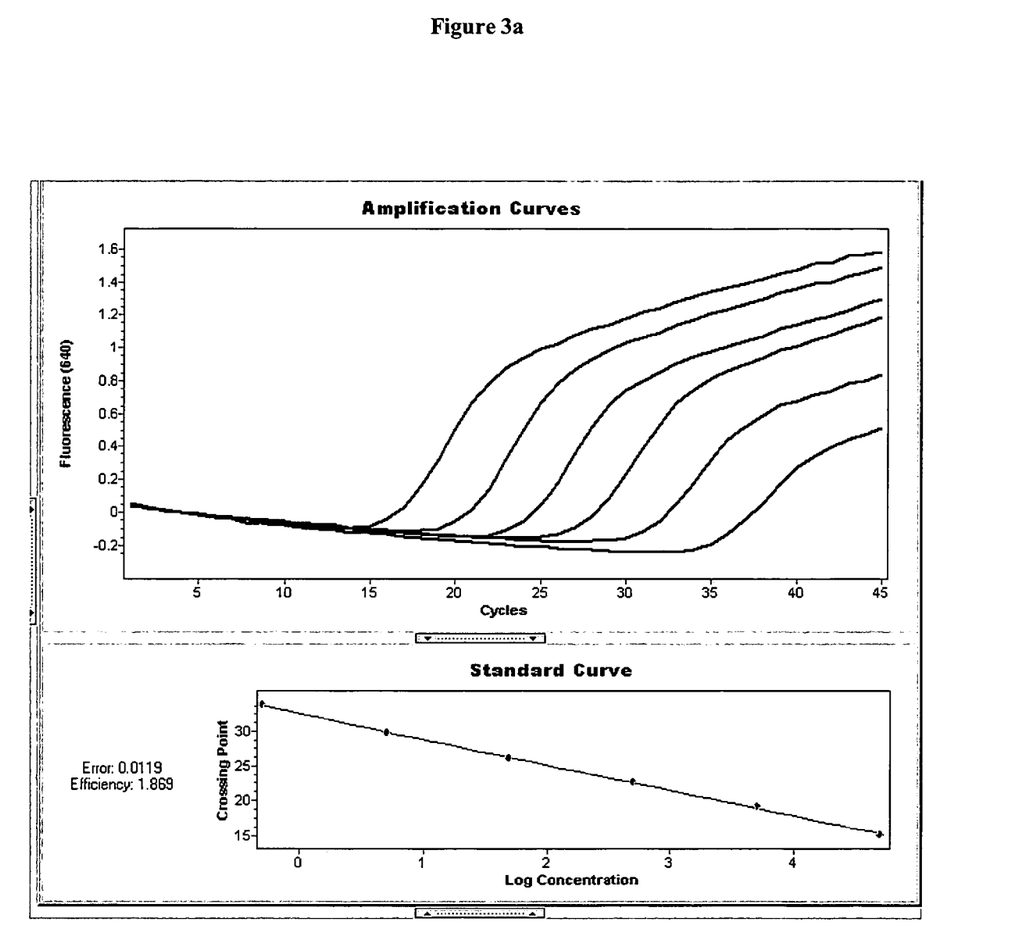
FIG. 3a: PCR efficiency without compound 1 or 2: 1.869
Figure 3B:
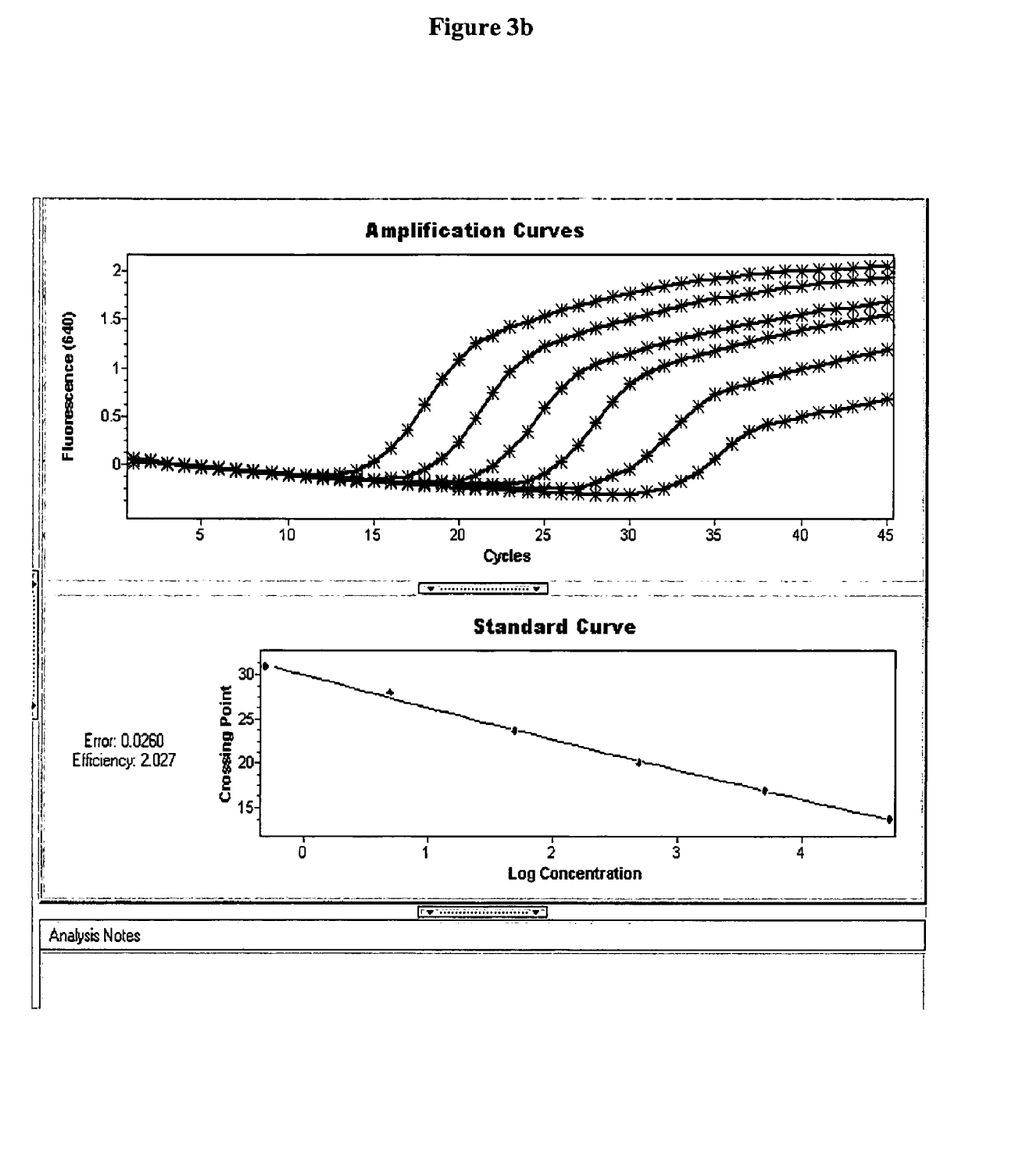
FIG. 3b: PCR efficiency with compound 2: 2.027
Figure 3C:
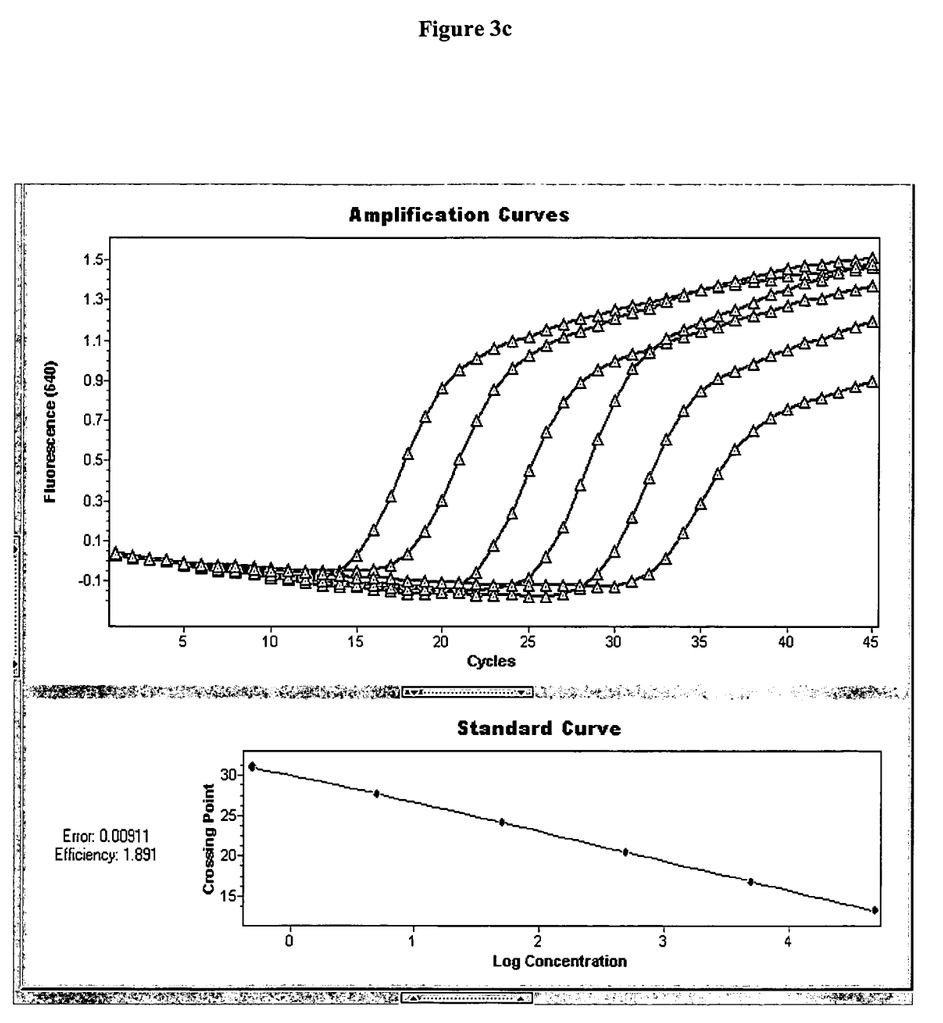
FIG. 3c: PCR efficiency with compound 1: 1.891

Reaction was monitored in real time and efficiency of the reaction was determined using the HYBPROBE modus 640 nm of the LIGHTCYCLER instrument according to the manufacturer's instructions. As can be seen in FIG. 3, amplification occurred with an efficiency of 1.841 per amplification cycle, if no additives were added (FIG. 3a). In contrast, amplification efficiency was increased in the presence of compound 1 to 1.891 per amplification cycle and 2.027 in the presence of Compound 2.

| Target conc. | Crossing point − additive | Crossing point + compound 1 | Crossing point + compound 2 |
|---|---|---|---|
| 50 pg | 15.09 | 13.34 | 13.69 |
| 5 pg | 19.14 | 16.72 | 16.95 |
| 500 fg | 22.59 | 20.47 | 20.06 |
| 50 fg | 26.25 | 24.13 | 23.66 |
| 5 fg | 29.94 | 27.52 | 27.76 |
| 0.5 fg | 32.85 | 30.08 | 30.47 |
| PCR efficiency | 1.869 | 1.891 | 2.027 |

Example 5

Reduction of Non Specific PCR Product Formation

For this experiment, a 10 fold generic primer mix was prepared for amplification of a sequence from the 16S region of gram positive bacteria using the following primers

```
Primer fwd
                                            (SEQ ID NO: 9)
(Sequence: 5'-GAA CCT TAC CAG ATC TTG ACA TCC-3')

Primer rev
                                           (SEQ ID NO: 10)
(Sequence: 5'-CCA TGC ACC ACC TGT CAC-3')
```

The primers were diluted to a concentration of 5 µM.

The detection was performed using SYBR Green ID-Nr.: 11988131001 in a 1:100 dilution in PCR-grade water.

As target Staphylococcus genomic DNA was used in the following way. A four serial single dilutions of the S. aureus DNA were prepared with concentrations of c=102 geq/50 µl, c=10 geq/50 µl, c=1 geq/50 µl and c=0.5 geq/50 µl in elution buffer (10 mM TRIS ph 8.3).

To simulate a sample preparation procedure from human blood 5 µg hDNA were spiked, (Roche Diagnostics GmbH, Catalog No 11691112001) to the standard dilutions.

As control experiment a PCR experiment without any target DNA (NTC=no template control) was performed.

Pipetting Scheme for Mastermix: for 36 Reactions in 100 µl Capillaries

| Component | Volume |
|---|---|
| H2O | 135.00 µl |
| MgCl2 (25 mM) | 432.00 µl |
| 1 a | 51.00 µl |
| 1 b | 669.00 µl |
| Primer fwd 5 µM/L | 252.00 µl |
| Primer rev 5 µM/L | 252.00 µl |
| SYBR Green (1:100 in water) | 9.00 µl |
| Volume | 1800 µl |

50 µl of the mastermix were pipetted in a 100 µl LC-capillary and 50 µl of the standard were added.

PCR was performed with LIGHTCYCLER 2.0 instrument (Roche Diagnosticsa GmbH, Mannheim) using a custom made DNA free master mix—LIGHTCYCLER UniTool 100 v.3 Kit (Roche Diagnostics GmbH, Mannheim, Cat. No. 03 585 727)—basically containing bottle 1a: Fast Start Enzym, bottle 1b: Reaction Mix 5×, bottle 2: $MgCl_2$ (25 mM) M-grade, bottle 3: $H_2O$, PCR-M-grade and bottle 16: Elution buffer for a 100 µl reaction.

Values for denaturation, amplification and melting curve analysis were programmed as follows:

Program 1: Denaturation

| Cycle Program Data | Value |
|---|---|
| Cycles | 1 |
| Analysis Mode | None |
| Temperature Targets | Segment 1 |
| Target temperature | 95 |
| Incubation time (min:s) | 10:00 |
| Temperature transition rate (° C./s) | 20 |
| Secondary target temperature (° C.) | 0 |
| Step size (° C.) | 0 |
| Step delay (cycles) | 0 |
| Acquisition mode | None |

Program 2: Amplification 1

| Cycle Program Data | Value | | |
|---|---|---|---|
| Cycles | 10 | | |
| Analysis Mode | None | | |
| Temperature Targets | Segment 1 | Segment 2 | Segment 3 |
| Target temperature | 95 | 60 | 72 |
| Incubation time (s) | 20 | 25 | 40 |
| Temperature transition rate (° C./s) | 20 | 20 | 20 |
| Secondary target temperature (° C.) | 0 | 0 | 0 |
| Step size (° C.) | 0 | 0 | 0 |
| Step delay (cycles) | 0 | 0 | 0 |
| Acquisition mode | None | None | Single |

Program 3: Amplification 2

| Cycle Program Data | Value | | |
|---|---|---|---|
| Cycles | 35 | | |
| Analysis Mode | Quantification | | |
| Temperature Targets | Segment 1 | Segment 2 | Segment 3 |
| Target temperature | 95 | 60 | 72 |
| Incubation time (s) | 20 | 25 | 40 |
| Temperature transition rate (° C./s) | 20 | 20 | 20 |
| Secondary target temperature (° C.) | 0 | 0 | 0 |
| Step size (° C.) | 0 | 0 | 0 |
| Step delay (cycles) | 0 | 0 | 0 |
| Acquisition mode | None | None | Single |

Program 4: Melting Curve

| Cycle Program Data | Value | | |
|---|---|---|---|
| Cycles | 1 | | |
| Analysis Mode | Melting curve | | |
| Temperature Targets | Segment 1 | Segment 2 | Segment 3 |
| Target temperature | 95 | 40 | 95 |
| Incubation time (s) | 0 | 60 | 60 |
| Temperature transition rate (° C./s) | 20 | 20 | 0.1 |
| Secondary target temperature (° C.) | 0 | 0 | 0 |
| Step size (° C.) | 0 | 0 | 0 |
| Step delay (cycles) | 0 | 0 | 0 |
| Acquisition mode | None | None | Cont |

Program 5: Cooling

| Cycle Program Data | Value |
|---|---|
| Cycles | 1 |
| Analysis Mode | None |
| Temperature Targets | Segment 1 |
| Target temperature | 40 |
| Incubation time (min:s) | 30 |
| Temperature transition rate (° C./s) | 20 |
| Secondary target temperature (° C.) | 0 |
| Step size (° C.) | 0 |
| Step delay (cycles) | 0 |
| Acquisition mode | None |

Reaction was monitored in real time using the SYBR Green modus of the LIGHTCYCLER instrument according to the manufacturer's instructions.

The validity of the PCR reaction was additionally performed by gel electrophoresis The Cp-values of the quantification curves of the LIGHTCYCLER experiment (not shown) confirmed the linearity and sensitivity of this experiment. The positive signal of the no template control (NTC) is a result of a primer/dimer formation and in the presence of hDNA of non specific PCR product formation. It could be distinguished from Staphylococcus PCR amplicon (83 bp) via melting curve analysis and by determination of the amplicon size in gel electrophoresis.

What is claimed is:

1. A method of decreasing nonspecific hybridization events in a solution comprising nucleic acid sequences, said method comprising the steps of:

provide a solution comprising nucleic acid sequences and adding a benzimidazolium compound or a salt of said benzimidazolium compound to the solution wherein the salt of the benzimidazolium compound has a structure wherein $R_1$ and $R_2$ are independently selected from the group consisting of H, C1 alkyl, C2 alkyl, C3 alkyl, C4 alkyl, —$(CH_2)_o$—O—$(CH_2)_p$—H, wherein o+p is ≦3, q is ≦6, and $R_3$ is selected from the group consisting of C1 alkyl, C2 alkyl, C3 alkyl, and C4 alkyl, with the proviso that $R_1$ and $R_2$ are not both H, and wherein the salt has a sulfonate or halogenide counterion.

2. The method of claim 1 wherein q is 4.

3. The method of claim 1 wherein the benzimidazolium compound has a structure wherein $R_1$ is selected from the group consisting of H, C1 alkyl, C2 alkyl, C3 alkyl, and C4 alkyl and $R_2$ is selected from the group consisting of C1 alkyl, C2 alkyl, C3 alkyl, and C4 alkyl.

4. The method of claim 1 wherein said solution further comprises components necessary for performing a nucleic acid amplification.

5. A method of decreasing nonspecific hybridization events in a solution comprising nucleic acid sequences, said method comprising the steps of:

providing a solution comprising nucleic acid sequences and adding a benzimidazolium compound or a salt of said benzimidazolium compound to the solution wherein the salt of the benzimidazolium compound has a structure wherein $R_1$ is C1-C4 alkyl and $R_2$ is C1-C6 alkyl wherein the distal C atom of $R_1$ or $R_2$ is substituted with an imidazole or benzimidazole group, and wherein the salt has a sulfonate or halogenide counterion.

6. The method of claim 5 wherein said benzimidazolium compound is 3-ethyl-1-[4-(3-ethyl-3H-benzimidazol-1-ium)-but-1-yl]3H-benzimidazol-1-ium or 3-methyl-1-[4-(3-methyl-3H-benzimidazol-1-ium)-but-1-yl]3H-benzimidazol-1-ium.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaggtccggc agcgtcagg                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcaggtcgc gacgcaacg                                                    19

<210> SEQ ID NO 3
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 3
caggtggaag gtgcgtccgt tg                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttctccctc tgtggccttc ac                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagagacatc gcctctgggc ta                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgttatcaca ctggtgctaa                                                 20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
aatacctgta ttcctcgcct gtc                                             23

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
agggatctgc tcttacagat tagaagtagt cctatt                               36

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
                                    -continued
    primer

<400> SEQUENCE: 9
gaaccttacc agatcttgac atcc                                           24

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccatgcacca cctgtcac                                                  18
```